(12) United States Patent
Nakaura et al.

(10) Patent No.: US 7,551,721 B2
(45) Date of Patent: Jun. 23, 2009

(54) X-RAY DIAGNOSTIC APPARATUS, IMAGE PROCESSING APPARATUS, AND PROGRAM

(75) Inventors: Takeshi Nakaura, 4-93, Idenakama 3-chome, Kumamoto-shi, Kumamoto-ken (JP); Satoru Ohishi, Otawara (JP)

(73) Assignees: Takeshi Nakaura, Kumamoto-shi (JP); Toshiba Medical Systems Corporation, Otawara-shi (JP)

( * ) Notice: Subject to any disclaimer, the term of this patent is extended or adjusted under 35 U.S.C. 154(b) by 142 days.

(21) Appl. No.: 11/676,885

(22) Filed: Feb. 20, 2007

(65) Prior Publication Data

US 2007/0195932 A1    Aug. 23, 2007

(30) Foreign Application Priority Data

Feb. 20, 2006    (JP) .............................. 2006-042665

(51) Int. Cl.
*A61B 6/00* (2006.01)
(52) U.S. Cl. .................................... 378/98.12; 382/130
(58) Field of Classification Search .............. 378/98.11, 378/98.12; 382/130; 600/425, 431
See application file for complete search history.

(56) References Cited

U.S. PATENT DOCUMENTS

| | | | |
|---|---|---|---|
| 4,903,705 A | 2/1990 | Imamura et al. | |
| 5,647,360 A | 7/1997 | Bani-Hashemi et al. | |
| 6,370,217 B1 * | 4/2002 | Hu et al. | 378/8 |
| 6,754,522 B2 * | 6/2004 | Keren | 378/98.11 |

FOREIGN PATENT DOCUMENTS

| | | |
|---|---|---|
| EP | 0 374 328 A1 | 6/1990 |
| FR | 2 782 629 | 3/2000 |
| JP | 2004-112469 | 4/2004 |
| WO | WO 03/094734 A2 | 11/2003 |
| WO | WO 2004/034329 A2 | 4/2004 |

* cited by examiner

*Primary Examiner*—Chih-Cheng G Kao
(74) *Attorney, Agent, or Firm*—Oblon, Spivak, McClelland, Maier & Neustadt, P.C.

(57) ABSTRACT

An X-ray diagnostic apparatus includes an image generating unit which generates a plurality of X-ray images by repeatedly radiographing a subject before and after injection of a contrast medium, a region detecting unit which detects a non-contrast region from a plurality of mask images before injection of the contrast medium and a plurality of contrast images after injection of the contrast medium, which constitute the plurality of X-ray images, a mask selecting unit which separately selects one mask image with respect to each of the contrast images on the basis of a correlation between the contrast image and the mask image upon localization to the non-contrast region, and a subtraction processing unit which generates a subtraction image by performing subtraction between the contrast image and the selected mask image.

10 Claims, 9 Drawing Sheets

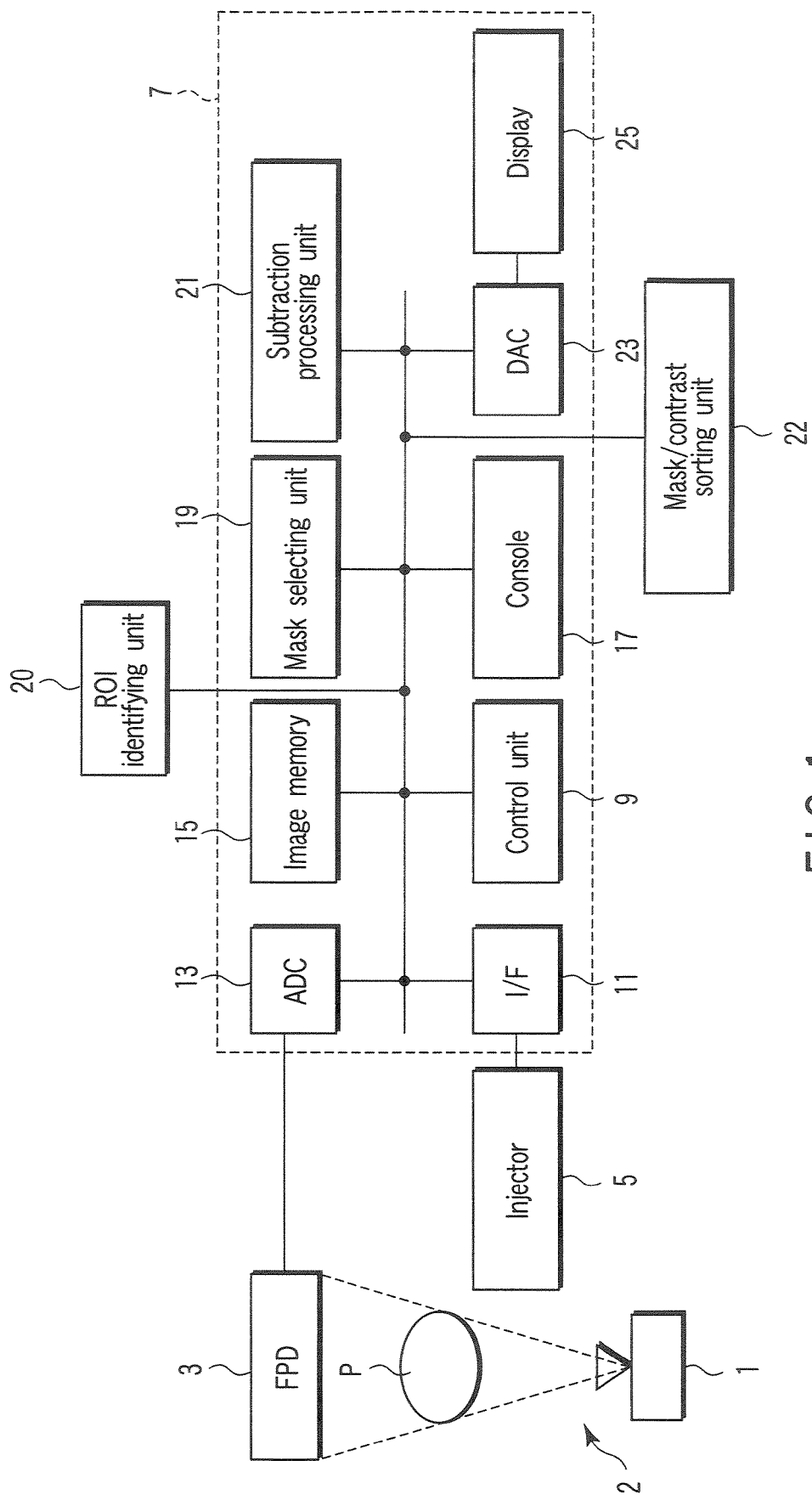
F I G. 1

US 7,551,721 B2

X-RAY DIAGNOSTIC APPARATUS, IMAGE PROCESSING APPARATUS, AND PROGRAM

CROSS-REFERENCE TO RELATED APPLICATIONS

This application is based upon and claims the benefit of priority from prior Japanese Patent Application No. 2006-042665, filed Feb. 20, 2006, the entire contents of which are incorporated herein by reference.

BACKGROUND OF THE INVENTION

1. Field of the Invention

The present invention relates to an X-ray diagnostic apparatus, image processing apparatus, and program which perform subtraction processing between images before and after the injection of a contrast medium.

2. Description of the Related Art

In performing DSA (Digital Subtraction Angiography) examination of an abdominal region, the patient is basically forced to temporarily hold his/her breath. However, normal DSA cannot be performed on a patient who cannot hold his/her breath, e.g., an elderly person, an infant, or an unconscious patient. Under the circumstances, there has been proposed a method of acquiring a larger number of mask images than that obtained by normal DSA, and selecting an optimal mask image, for each contrast image, which is similar in tissue movement to the contrast image from the acquired mask images, thereby obtaining a DSA image with only a blood vessel being enhanced while suppressing motion artifacts caused by the respiration of the patient (see Jpn. Pat. Appln. KOKAI Publication No. 2004-112469).

This method gives consideration to a region with much movement in determining an optimal mask image, and determines an optimal mask by comparison with a contrast image upon localization to the region.

However, a great shift may sometimes occur. This shift occurs because this method makes a blood vessel coincide with the bone structure of a mask image so as to reduce the influence of a signal based on the blood vessel which does not exist in the mask image. See Jpn. Pat. Appln. KOKAI Publication No. 2004-112469.

BRIEF SUMMARY OF THE INVENTION

It is an object of the present invention to reduce artifacts due to positional shifts caused by the body movement of a subject which occurs when subtraction processing is performed between images before and after the injection of a contrast medium.

According to an aspect of the present invention, there is provided an X-ray diagnostic apparatus comprising an image generating unit which generates a plurality of X-ray images by repeatedly radiographing a subject before and after injection of a contrast medium, a region detecting unit which detects a non-contrast region from a plurality of mask images before injection of the contrast medium and a plurality of contrast images after injection of the contrast medium, which constitute the plurality of X-ray images, a mask selecting unit which separately selects one mask image from the plurality of mask images with respect to each of the contrast images on the basis of a correlation between the contrast image and the mask image upon localization to the non-contrast region, and a subtraction image generating unit which generates a subtraction image by performing subtraction between the contrast image and the selected mask image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray diagnostic apparatus according to an embodiment of the present invention;

DETAILED DESCRIPTION OF THE INVENTION

Figure 2:
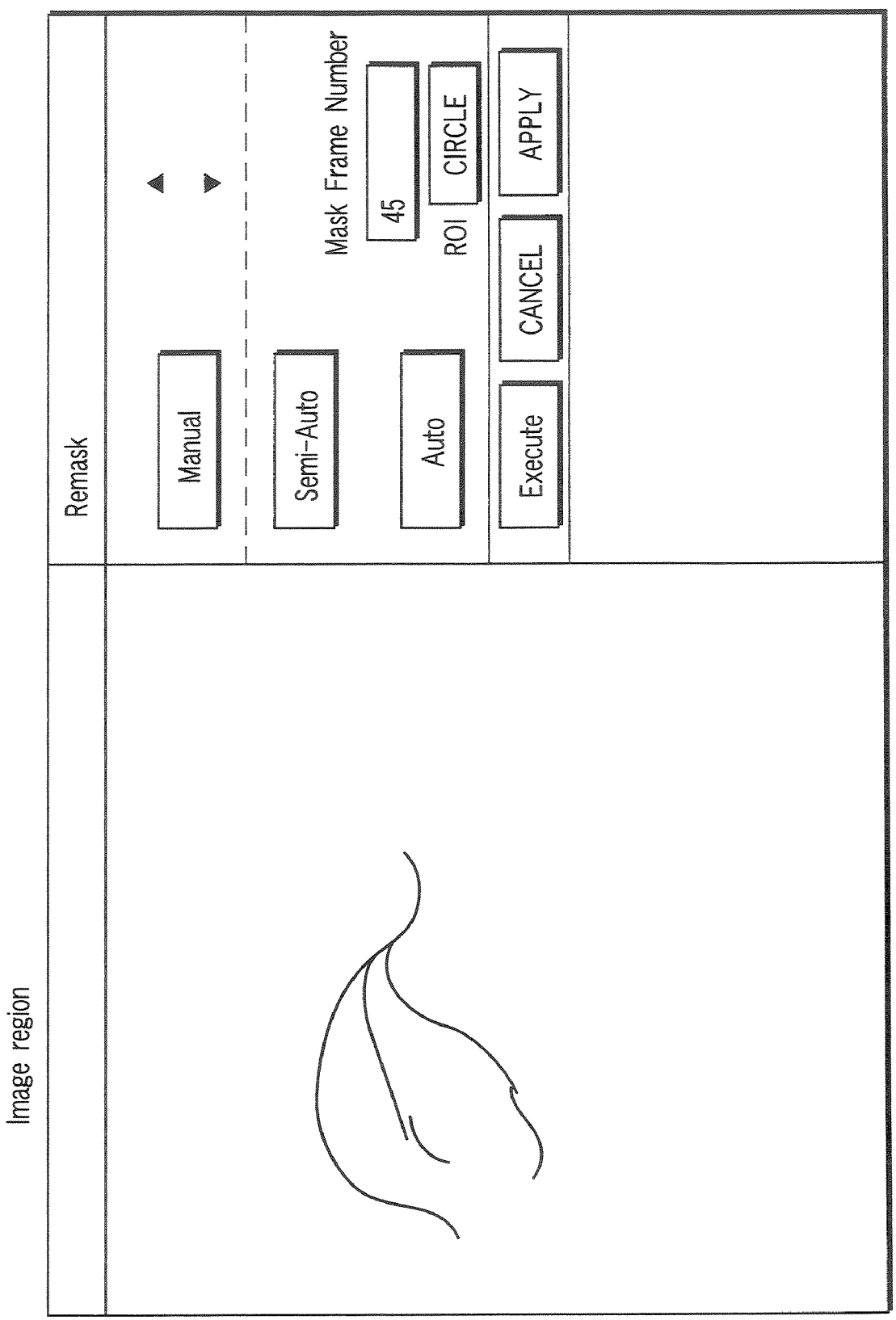
FIG. 2 is a view showing an example of an initial window in this embodiment.

A preferred embodiment of the present invention will be described below with reference to the views of the accompanying drawing. Note that the present invention includes an image diagnostic apparatus which can acquire contrast images. This type of image diagnostic apparatus includes an X-ray diagnostic apparatus, ultrasonic diagnostic apparatus, magnetic resonance imaging apparatus, PET, and SPECT. Any of these apparatuses can be applied to the present invention. The following will exemplify an X-ray diagnostic apparatus.

FIG. 1 shows the arrangement of an X-ray diagnostic apparatus according to this embodiment. An image acquisition unit 2 includes an X-ray tube 1 and an X-ray detector 3 which face each other through a subject P placed on a bed. The X-ray tube 1 and the X-ray detector 3 are supported by a "C"-shaped arm (not shown). This arm has three or more axes of rotation and is arbitrarily rotatable around them. The subject P can be observed from various directions by moving the X-ray tube 1 and X-ray detector 3 by utilization of the rotation of the arm.

This apparatus uses a flat panel detector (FPD) including a scintillator and a photodiode array as the X-ray detector 3. However, the apparatus may use a combination of an image intensifier and a TV camera as the X-ray detector 3. An injector 5 is a device for automatically injecting a contrast medium into the subject P. This device can inject a contrast medium and stop the injecting operation in accordance with control signals from a control unit 9. Since the injector 5 operates under the control of the control unit 9, the operator can designate the time from the start of radiography to the injection of a contrast medium, i.e., the acquisition time for mask images, through the console 17, and can make the injector 5 automatically start injecting the contrast medium when the designated acquisition time has elapsed from the start of radiography.

An image processing apparatus 7 receives an analog video signal of an X-ray image output from the X-ray detector 3 through an analog/digital converter 13. In addition to an injector interface 11 and the analog/digital converter 13, the image processing apparatus 7 comprises the control unit 9, an image memory 15 which stores image data and the like, a console 17, a mask selecting unit 19, an ROI identifying unit 20, a subtraction processing unit 21, a mask/contrast sorting unit 22, a digital/analog converter 23, and a display 25.

The mask/contrast sorting unit 22 sorts a plurality of X-ray images acquired by the image acquisition unit 2 into a plurality of mask images before the injection of the contrast medium and a plurality of contrast images after the injection of the contrast medium. A sorting method to be used may be a method of sorting/designating a sequence of X-ray images into the above two types in accordance with an instruction input from the operator through the console 17 or a method based on automatic sorting. When, for example, automatic sorting is applied to the heart, the apparatus generates a plurality of subtraction images with different electrocardiographic phases by performing subtraction between pairs of X-ray images, of a plurality of X-ray images whose electrocardiographic phases are nearest to each other, and sorts the plurality of X-ray images into mask images and contrast images on the basis of temporal changes in the pixel values of the plurality of subtraction images.

The ROI identifying unit 20 detects a region (to be referred to as a non-contrast region hereinafter) which is almost free from the influence of the contrast medium and hardly undergoes a change in density before and after the injection of the contrast medium on the basis of a plurality of mask images before the injection of the contrast medium and a plurality of contrast images after the injection of the contrast medium which constitute the plurality of X-ray images acquired by the image acquisition unit 2. Although described in detail later, the ROI identifying unit 20 generates a first minimum value projection image from a plurality of mask images by projection processing in the time-axis direction, generates a second minimum value projection image from a plurality of contrast images, and detects a non-contrast region on the basis of a subtraction image between the first minimum value projection image and the second minimum value projection image.

The mask selecting unit 19 selects an optimal one of the mask images acquired before the injection of the contrast medium for each of the contrast images acquired after the injection of the contrast medium. Although described in detail later, in brief, the mask selecting unit 19 calculates the correlation between a given contrast image and each of a plurality of mask images upon localization to the non-contrast region detected by the ROI identifying unit 20, and selects, as an optimal mask image, a mask image exhibiting the least positional shift between tissues except for a change due to the contrast medium for each contrast image. This makes it possible to reduce an artifact due to a positional shift on the subtraction image which is caused by the body movement of the subject. This artifact is a false image produced by a subtraction computation residue due to the positional shift.

The subtraction processing unit 21 generates a subtraction image by performing subtraction between a contrast image and a selected mask image. The display 25 receives the subtraction image through the digital/analog converter 23 or directly displays it.

Mask selecting operation according to this embodiment will be described below. A specific case for an abdominal region will be described first. This mask selecting operation may be the operation of selecting an optimal one of a plurality of mask images for each contrast image, or may be applied to another technique as a preliminary stage, e.g., a so-called re-mask stage of tentatively selecting a mask image, for each contrast image, which is regarded to have an equivalent phase upon rough measurement of a respiratory phase by another method, initially generating a plurality of subtraction images by subtraction between the respective pairs, and redoing the processing from the selection of mask images from the subtraction images with respect to contrast images exhibiting large body movement artifacts, in particular. The following will exemplify the application of the operation to the re-mask stage.

This apparatus acquires contrast blood vessel images by using a special program for abdominal regions, which is designed for radiography under respiration. This program performs mask image acquisition at, for example, 10 fps (frame/sec) for 5 sec, and then performs contrast image acquisition at 3 fps. The control unit 9 transmits the mask acquisition time to the injector 5. The injector 5 sets 5 sec as a delay time. At the start time of image acquisition (when an X-ray trigger is turned on), the control unit 9 transmits a radiography start signal to the injector 5. The injector 5 starts injecting a contrast medium after the lapse of 5 sec from the reception of the radiography start signal. The operator turns off the X-ray trigger when the purpose is achieved. The image memory 15 stores the data of a plurality of X-ray images acquired before and after the injection of the contrast medium.

FIG. 2 shows an example of a check window for a subtraction image upon initial mask image selection. If body movement artifacts have excessively occurred on the subtraction image, three types of modes are prepared for re-mask processing. The three types of modes include a manual mode (a mode of manually selecting an optimal mask image), a semi-automatic mode (a mode of selecting an optimal mask image partly manually), and an automatic mode (a mode of automatically selecting an optimal mask image without any manual operation throughout the entire process).

First of all, in setting the manual mode, when the operator turns on the manual button (Manual) while a re-mask target contrast image is displayed (or a subtraction image between the initial mask image and a contrast image is displayed), the button is set in the depressed state. In this state, manual re-mask processing is made valid. When the operator presses this button again, the button returns to the initial projected state, and manual re-mask processing is made invalid. While this processing is valid, the operator can visually check a subtraction image based on each mask image by sequentially changing the mask images by operating the up (↑) and down (↓) keys of the keyboard. Alternatively, the operator can perform the same processing by pressing the buttons located beside the manual button. The operator selects a corresponding mask image from a plurality of mask images. The plurality of mask images are images radiographed before the injection of the contrast medium. In this case, the initial 50 frames correspond to them. When the operator changes the mask image, the frame number (1 to 50) of the mask image is displayed like "mask: k" on the upper left of the image (when the kth frame corresponds to a mask image). As the operator presses the up key, the frame number changes like "k+1" and "k+2". Likewise, as the operator pressed the down key, the frame number changes like "k−1" and "k−2". Upon selecting an optimal mask image, the operator presses the execution (Execute) key to confirm the mask image. Operating this execution key will make subsequent frames be displayed on the basis of the results obtained by applying the confirmed mask image.

Figure 3:
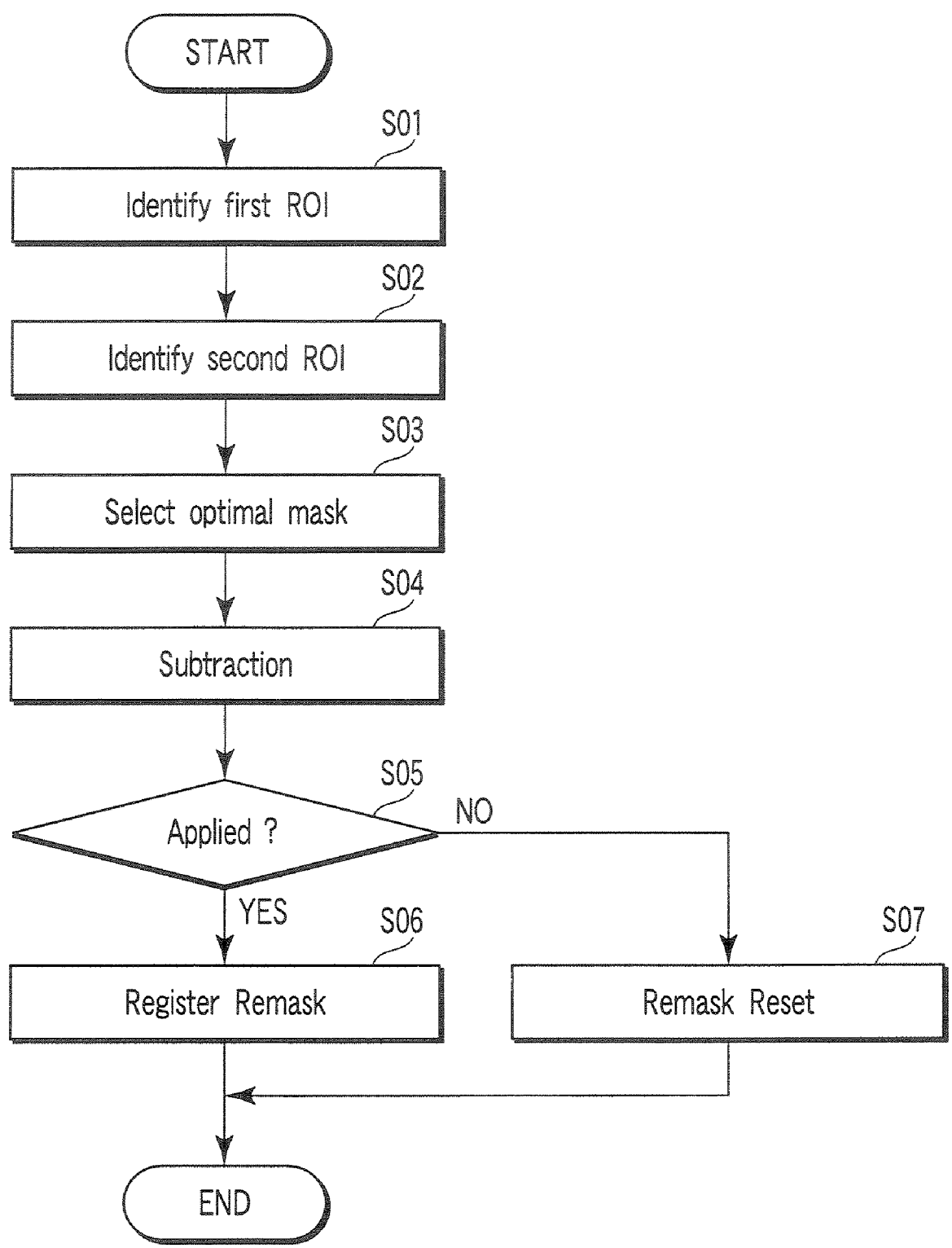
FIG. 3 is a flowchart showing a semi-automatic processing procedure in this embodiment.
Figure 4A:
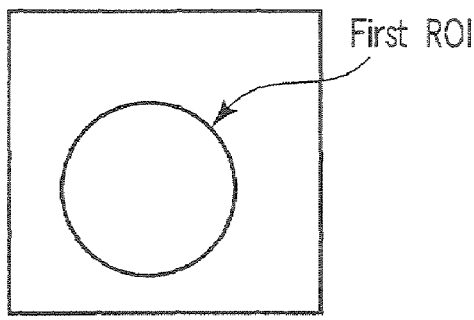
FIGS. 4A to 4F are supplementary views for second ROI detection processing in FIG. 3.

FIG. 3 shows a re-mask processing procedure in the semi-automatic mode. In setting the semi-automatic mode, when the operator turns on the semi-automatic button (Semi-auto), the button is set in the depressed state. In this state, re-mask processing in the semi-automatic mode is made valid. When the operator presses this button again, the button returns to the initial projected state. The semi-automatic re-mask processing is then made invalid. First of all, when a re-mask target image is displayed (assume that the re-mask target image is the $l_0$th image), semi-automatic re-mask processing is made valid, and an ROI mark representing a region of interest (ROI) is displayed on the image. The operator can select a rectangular shape, a circular shape, or the like for this ROI mark. For example, the circular ROI mark is displayed on the image (see FIG. 4A). The operator can move and enlarge/reduce this ROI mark by an arbitrary graphics drawing function. Note that the region of interest ROI will be referred to as a first ROI so as to be discriminated from an ROI (second ROI) to be described later. The operator sets the first ROI so as to enclose a region where a noticeable body movement artifact has occurred by using the ROI mark through the console 17 (S01).

Figure 4B:
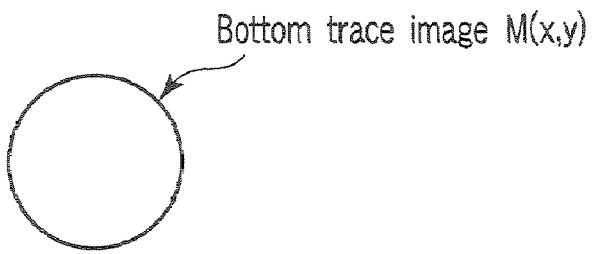
Figure 4C:
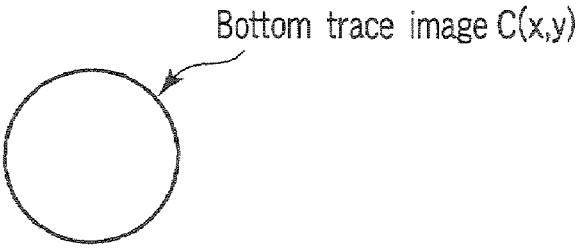
Figure 4D:
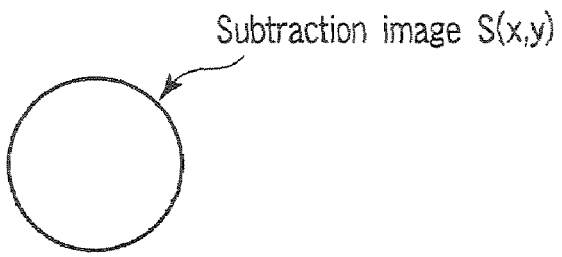
Figure 5:
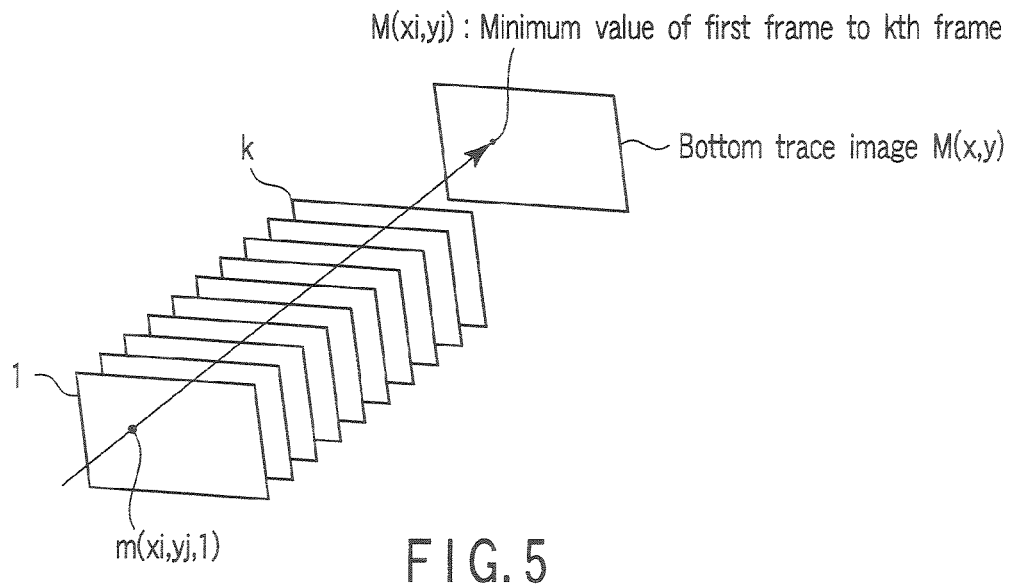
FIG. 5 is a supplementary view for bottom trace image generation in FIG. 4.

The operator presses the execution key to detect an optimal mask image. When the operator presses the execution key, the apparatus generates the bottom trace image in FIG. 4B in the following manner upon localization to the inside of the first ROI (see FIG. 5). A bottom trace image is obtained by searching a plurality of images at different radiography times for a pixel value in the time direction for every coordinates, and setting the minimum value as a pixel value at the corresponding coordinates on a minimum value projection image. This image is generally called MinIP. The radiographic region of the bottom trace image is covered by all mask images.

$$M(x, y) = \underset{k=1\ ROI}{\overset{K}{\text{MIN}}} \{m(x, y, k)\} \quad (1)$$

where m(x, y, l) represents a mask image, m(x, y, k) is the pixel value at the (x, y) coordinates (x, y: 1 to N, N=1024 in general) at the kth frame, and MIN represents the operation of obtaining a minimum value at every (x, y) coordinates up to the frame represented by k=1 to K (representing the number of frames, 50 in this case). This operation is performed only within the first ROI. The apparatus then generates the bottom trace image in FIG. 4C in the following manner with respect to a contrast image.

$$C(x, y) = \underset{l=1\ ROI}{\overset{L}{\text{MIN}}} \{c, (x, y, l)\} \quad (2)$$

where c(x, y, k) represents a contrast image, c(x, y, 1) is the pixel value at the (x, y) coordinates at the first frame, and MIN represents the operation of obtaining a minimum value at every (x, y) coordinates up to the frame represented by l=1 to L (representing the number of frames, 100 in this case). This operation is performed only within the first ROI. The apparatus generates a subtraction image (FIG. 4D) between the generated bottom trace image of the contrast image and the bottom trace image of the mask image in the following manner.

$$S(x, y) = -\log_e\left(\frac{C(x, y)}{M(x, y)}\right) \quad (3)$$

Figure 4E:
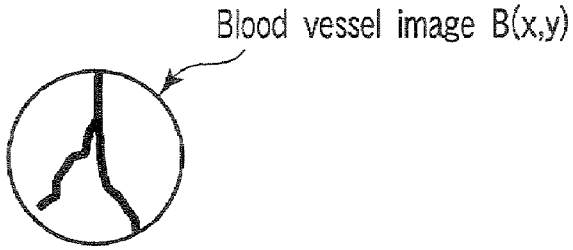
Figure 4F:
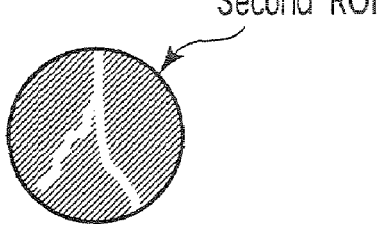

Using a threshold process for a subtraction image S(x, y) between the bottom trace image of the contrast image and the bottom trace image of the mask image makes it possible to detect a blood vessel region with high accuracy (FIG. 4E). As shown in FIG. 4F, removing the detected blood vessel region from the first ROI defined above allows to define a new second ROI (S02). This region of interest will be expressed as an ROI 2.

In the optimal mask detection step (S03), the apparatus sequentially performs correlation computation for an arbitrary contrast image c(x, y, l) to detect an optimal mask image. The apparatus determines a mask image exhibiting the lowest correlation computation result as an optimal mask image. Note that "the lowest correlation computation result" indicates that the images are most approximate to each other in terms of the spatial position of tissue or the like within a non-contrast region, i.e., the images exhibit the highest correlation. Depending on the calculation method to be used, a mask image exhibiting the highest correlation computation result is determined as an optimal mask image. This correlation computation can be written as follows:

$$CR_{l_0}(k) = \sum_{i=1}^{N}\sum_{j=1}^{N}[r2\{c(x, y, l_0) - m(x, y, k)\}]^2 \quad (3)$$

where c(x, y, $l_0$) and m(x, y, k) are respectively the contrast image of the $l_0$th frame and the mask image of the kth frame, N is the matrix size of the image, and $CR_{l_0}(k)$ is the correlation computation result. This apparatus obtains correlation computation results from k=1 to K, and determines a mask image exhibiting the minimum correlation computation result as an optimal mask image. In addition, r2 (x) is defined as follows:

$$r2(x) = \begin{cases} x: \text{inside } ROI2 \\ 0: \text{outside } ROI2 \end{cases}$$

In this case, the following processing will be described on the assumption that $k_0$ corresponds to a mask image which minimizes $CR_l'(k)$. In subtraction step S04, the apparatus performs subtraction between the contrast image c(x, y, l') and a mask image m(x, y, $k_0$). The apparatus displays the subtraction result. When the observer approves the result and presses the execution button, the apparatus registers, for example, a frame number $k_0$ identifying an optimal mask image for the contrast image of the l' th frame in a region attached to the DSA image (S06). The apparatus displays the registered optimal mask image by using the result obtained by applying the re-mask processing when the same image is displayed next. If the observer does not approve the result and presses the cancellation button, the apparatus erases the result (07). When the same processing is to be applied to a subsequent frame after the observer approves the result, the observer presses the application button (S05).

Figure 6:
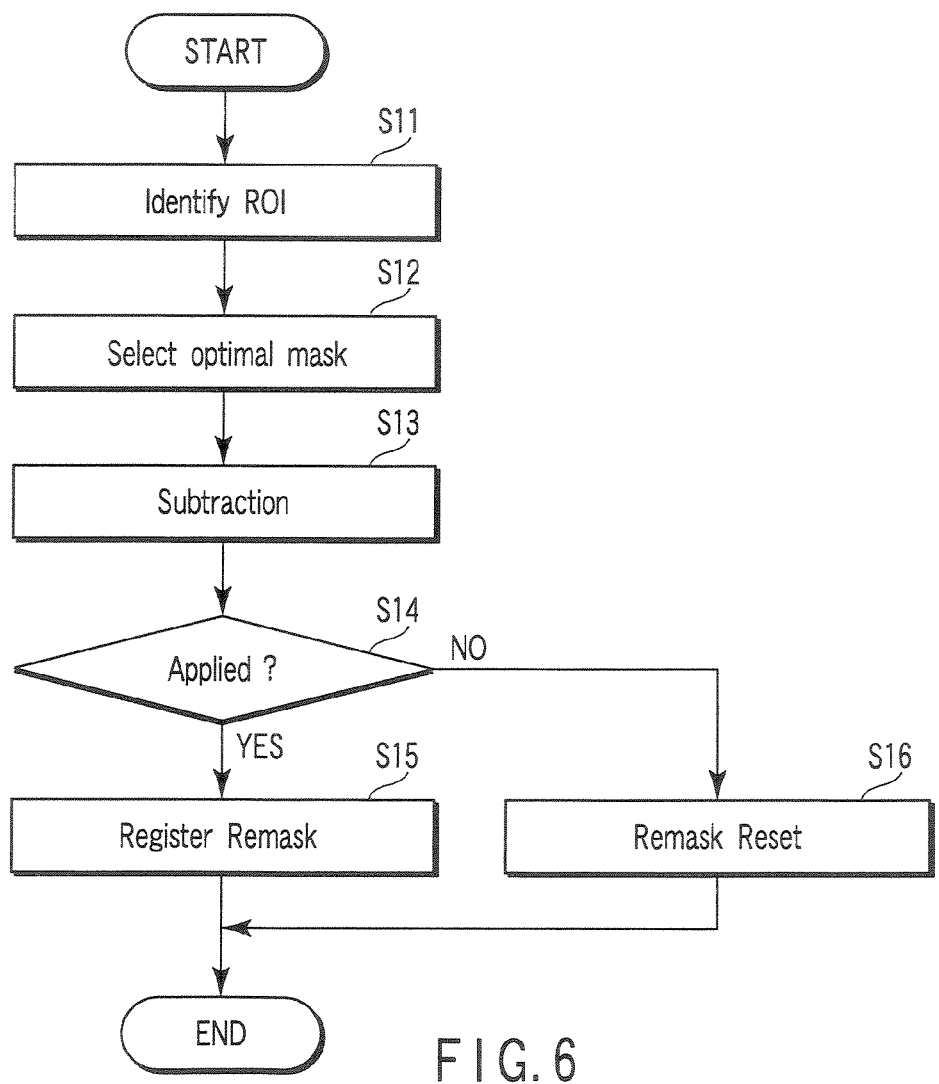
FIG. 6 is a flowchart showing an automatic processing procedure in this embodiment.

In setting the automatic mode, when the operator presses the automatic button, the button is set in the depressed state, and the apparatus starts processing. When the processing is complete, the button returns to the initial state. FIG. 6 shows a specific flowchart for this processing. First of all, the operator presses the automatic button after a re-mask target image is displayed (assume that the re-mask target image is the l' th image). Upon starting the processing, the apparatus detects an ROI first (S11). In the ROI detection step, the apparatus generates a bottom trace image of a mask image and a bottom trace image of a contrast image in the same manner as that indicated by equations (1) and (2). The apparatus uses equations (1) and (2) to generate bottom trace images only within the first ROI. In this case, however, the apparatus performs the processing for the entire image. The apparatus obtains a subtraction image between the generated bottom trace image of the contrast image and the bottom trace image of the mask image according to equation (3), and detects an ROI by performing a threshold process for the obtained subtraction image (S11).

Subsequent steps S12 to S16 respectively correspond to steps S03 to S07. The subsequent processing is performed in the same manner as in the semi-automatic mode.

According to this embodiment, selecting an optimal mask image upon localization to a non-contrast image region upon removal of a region influenced by a contrast medium makes it possible to prevent false recognition of body movement due to the influence of the contrast medium and reduce artifacts due to positional shifts caused by the body movement of the subject which occurs when subtraction processing is performed between images before and after the injection of the contrast medium.

(Specific Processing)

Figure 9A:
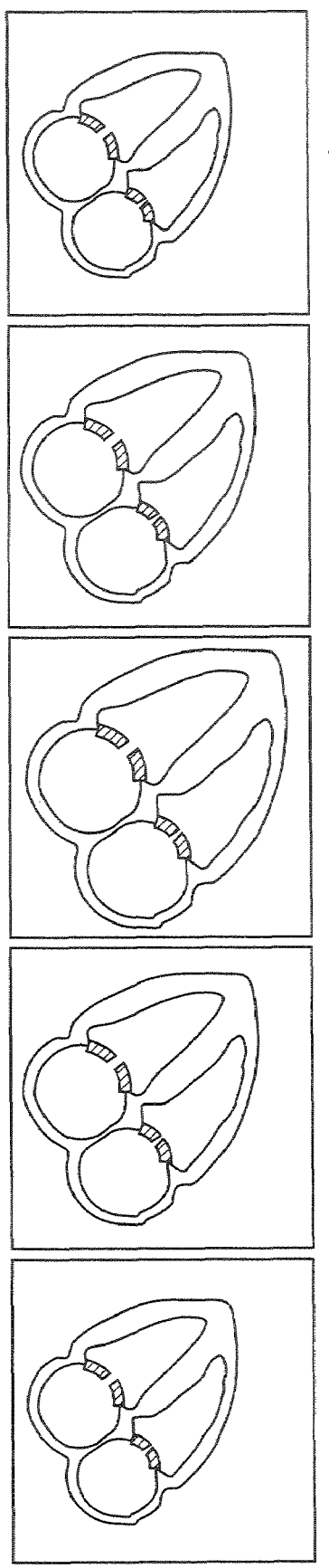
FIG. 9A is a view showing original mask images handled in optimal mask selection step S03 in FIG. 3.
Figure 9B:
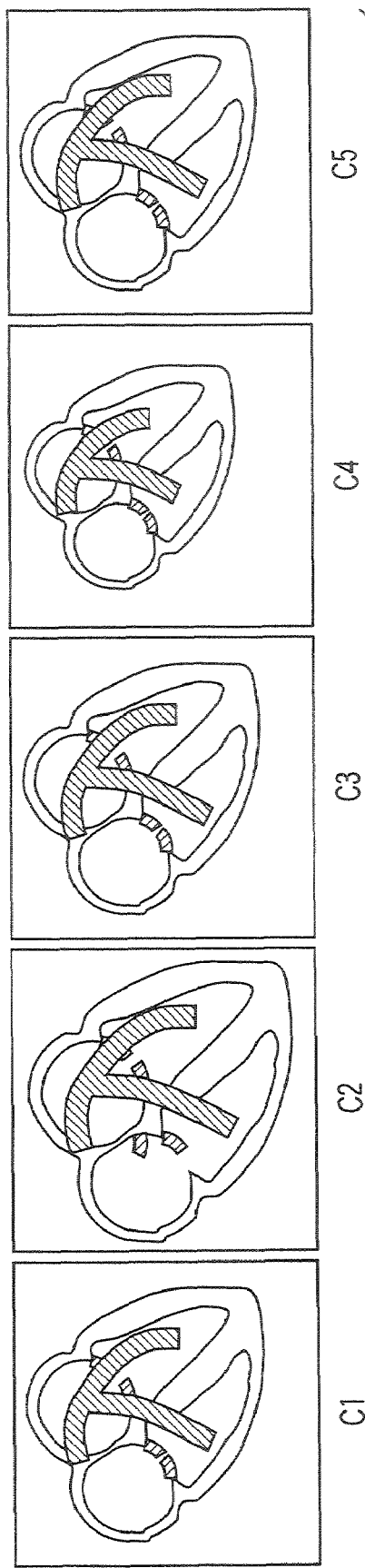
FIG. 9B is a view showing original contrast images handled in optimal mask selection step S03 in FIG. 3.

A specific example of mask image selection according to this embodiment will be described below. FIG. 9A shows original mask images M1 to M5. FIG. 9B shows original contrast images C1 to C5. The purpose of this processing is to select a mask image exhibiting the minimum positional shift due to body movement from the mask images M1 to M5 for each of the contrast images C1 to C5.

First of all, the apparatus generates bottom trace images (to be referred to as mask MinIPs) with respect to the mask images M1 to M5. Likewise, the apparatus generates bottom trace images (to be referred to as contrast MinIPs) with respect to the contrast images C1 to C5.

The apparatus then subtracts the contrast MinIPs from the mask MinIPs. This will extract a contrast region covering the contrast images C1 to C5. That is, this processing extracts a global contrast region which covers the contrast region of the contrast image C1, the contrast region of the contrast image C2, the contrast region of the contrast image C3, the contrast region of the contrast image C4, and the contrast region of the contrast image C5.

Figure 10A:
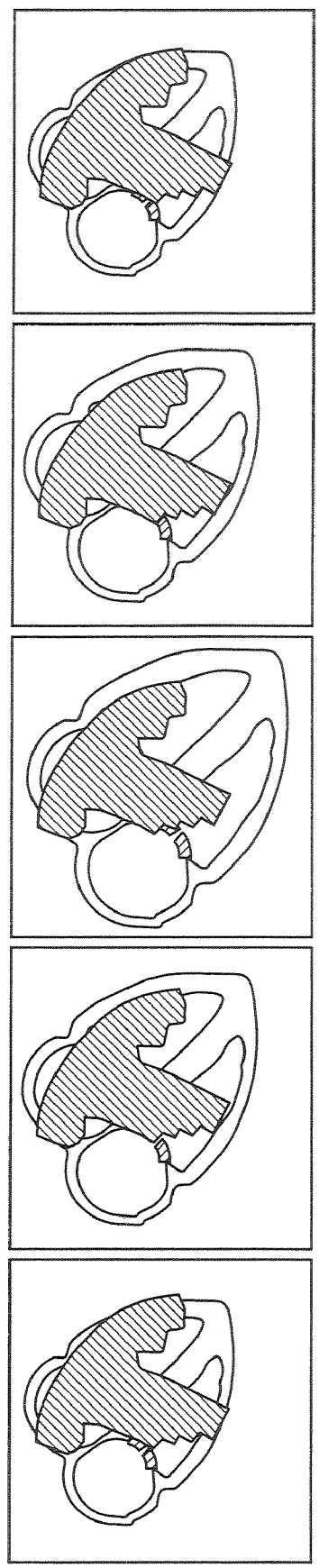
FIG. 10A is a view showing mask images from which blood vessel regions are removed in step S03 in FIG. 3.
Figure 10B:
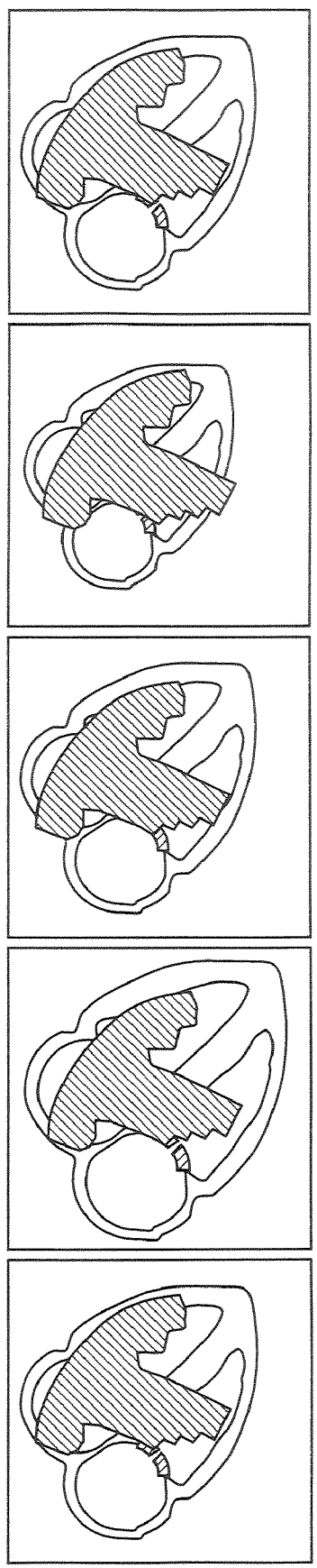
FIG. 10B is a view showing contrast images from which blood vessel regions are removed in step S03 in FIG. 3.

The apparatus then removes this global contrast region from each of the original mask images M1 to M5 and from each of the contrast images C1 to C5. Referring to each of FIGS. 10A and 10B, the hatching indicates the removed global contrast region. The apparatus calculates the correlations between all combinations of the mask images M1 to M5 and the contrast images C1 to C5 upon localization to the remaining regions (ROIs).

Figure 11:
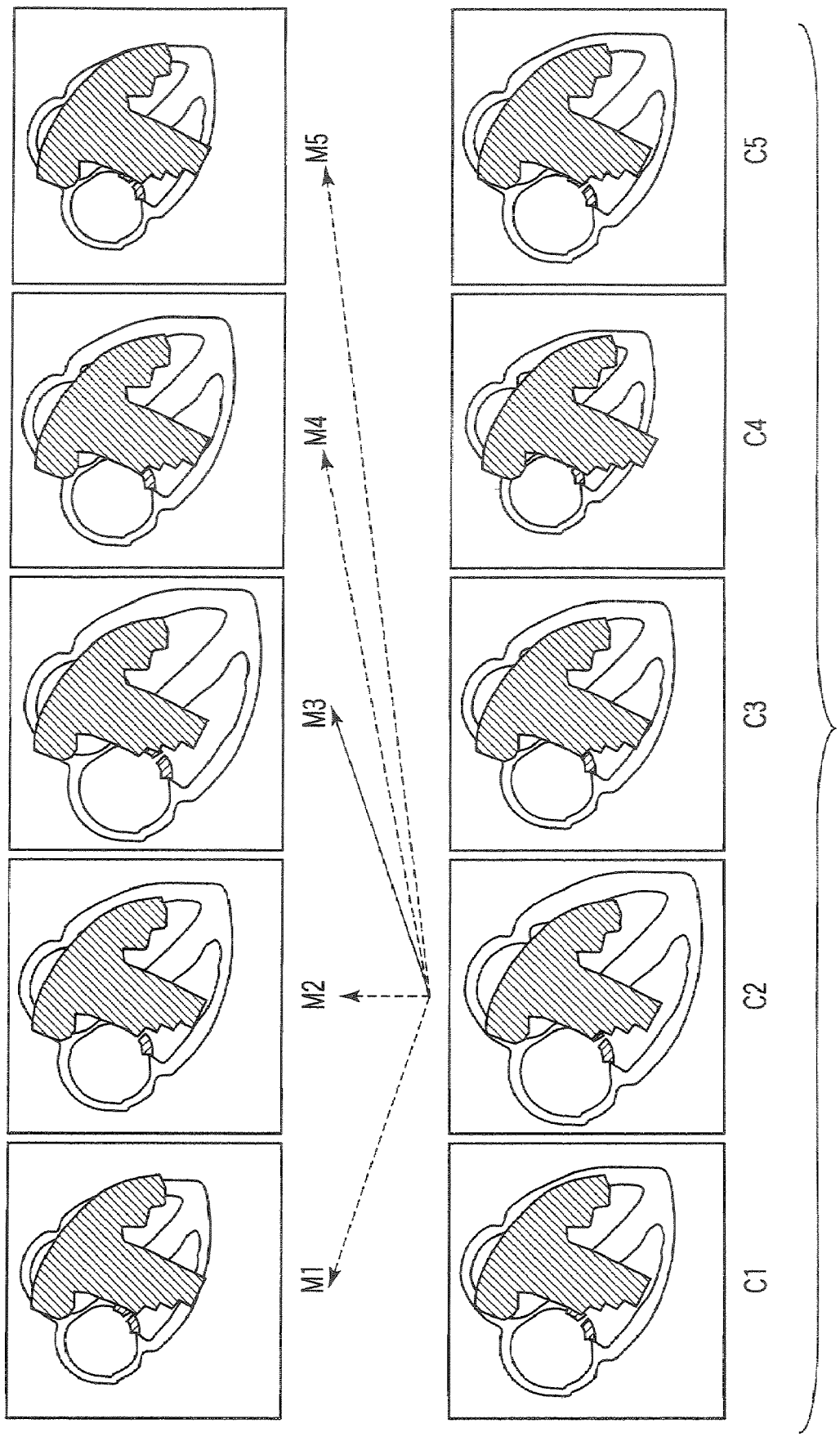
FIG. 11 is a view showing that a mask image M3 is selected with respect to a contrast image M2 in step S03 in FIG. 3.

The apparatus separately selects an optimal mask image from the mask images M1 to M5 for each of the contrast images C1 to C5 on the basis of the correlations. For example, as shown in FIG. 11, the apparatus selects the mask image M3 as an optimal mask image for the contrast image C2. Obviously, an optimal mask image is a mask image exhibiting the minimum positional shift with respect to the contrast image.

(First Modification)

The above embodiment automatically sorts acquired images into mask images and contrast images by using the delay time in the injector 5. When, however, an injection syringe is used to inject a contrast medium, it is difficult to inject the contrast medium in a predetermined period of time. It therefore suffices to sort acquired images into mask images and contrast images after image acquisition by inputting the number of frames of mask images in the item of the frame numbers of mask images. Notifying the timing of injection of a contrast medium using an injection syringe by displaying an injection start signal (icon or characters) on a monitor in an examination room can prevent failures.

(Second Modification)

This embodiment can also be applied to a case of the heart. In order to acquire contrast blood vessel images, the apparatus selects a special program for the heart. This program acquires mask images at 60 fps for 2 sec, and acquires contrast images at 30 fps. The X-ray diagnostic apparatus transmits the mask acquisition time to the injector 5. The injector 5 sets 2 sec as a delay time. At the start time of image acquisition (when an X-ray trigger is turned on), the control unit 9 transmits a signal to the injector 5. The injector 5 starts injecting a contrast medium after the lapse of 2 sec from the reception of the signal. The operator turns off the X-ray trigger when the purpose is achieved. The image memory stores the contrast images after the injection of the contrast medium. As shown in FIG. 2, there are three types of modes for re-mask processing, i.e., the manual mode, the semi-automatic mode, and the automatic mode. The operator uses the manual mode when it is necessary to perform re-mask processing after the completion of processing by the semi-automatic mode or automatic mode.

The processes performed in the semi-automatic mode, automatic mode, and manual mode are the same as those described above. However, in the case of examination on the heart, the operator often performs radiography in the extended viewing angle mode to perform precise observation. In such radiography, sometimes large blood vessels are radiographed first, and then the bed is moved to follow the flow of a contrast medium to peripheral blood vessels. In such a case, the apparatus detects the movement of the bed, sorts contrast images ranging from the contrast image of the first frame to the frame immediately before the detection of the movement of the bed as first contrast images and the subsequent contrast images as second contrast images, and applies this re-mask processing to only the first contrast images.

Although only the movement of the bed is described here, it suffices to detect the movement of the arm, the operation of the collimator, the operation of the compensation filter, or the like and define contrast images up to the time of detection as first contrast images.

In addition, although contrast images are automatically sorted into first contrast images and second contrast images, the operator may manually sort them (by, for example, inputting contrast frame numbers below the mask frame numbers in FIG. 2) as in the operation of sorting images into mask images and contrast images.

(Third Modification)

Figure 7:
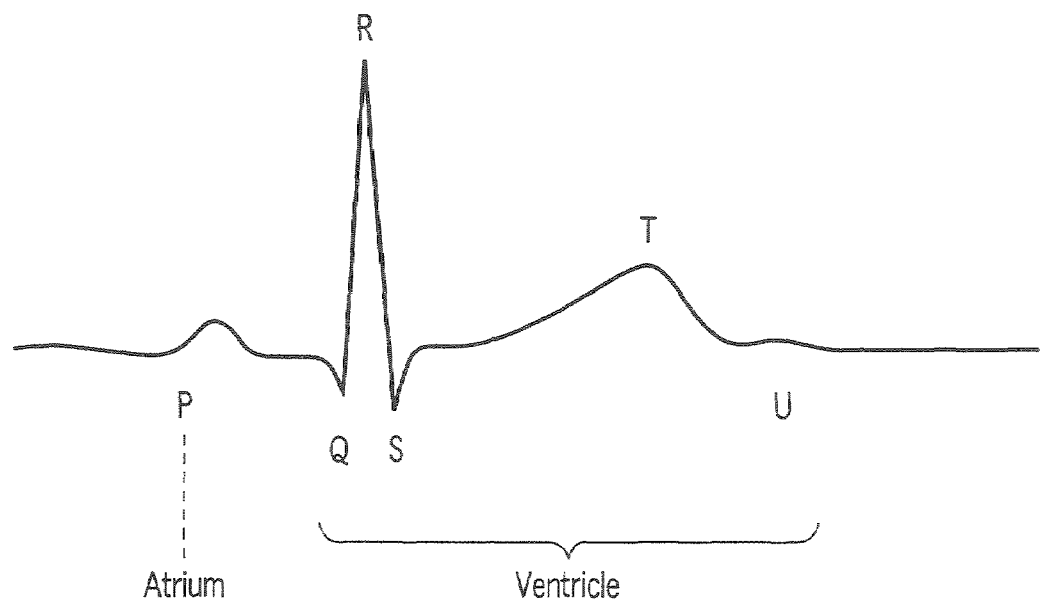
FIG. 7 is a view showing an electrocardiographic waveform for supplementarily explaining automatic sorting of mask images and contrast images in a modification to this embodiment.
Figure 8:
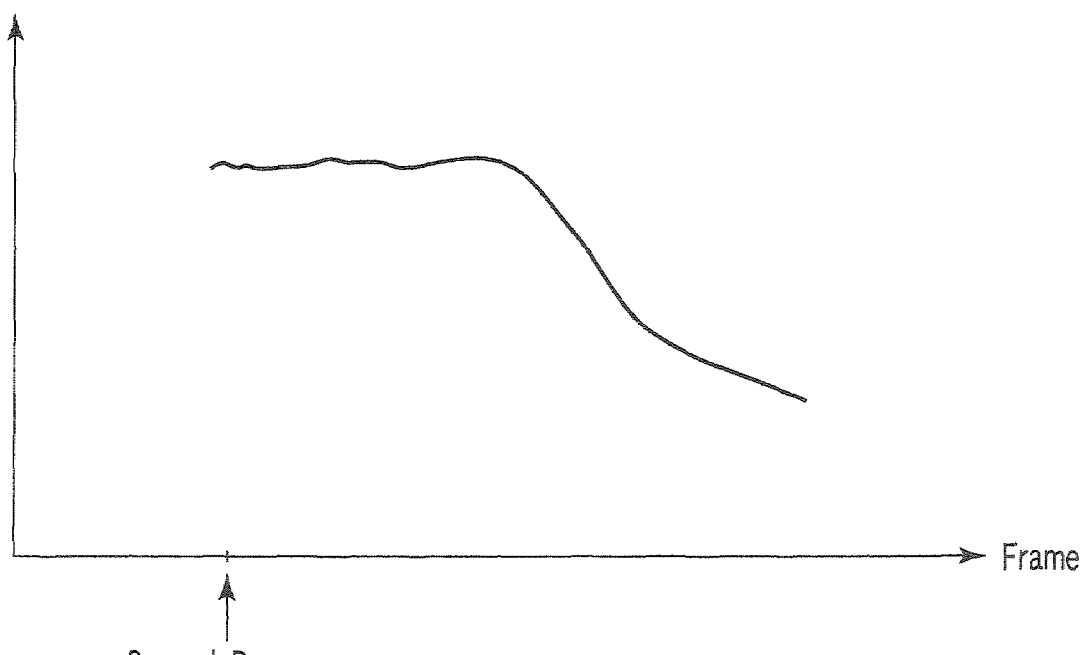
FIG. 8 is a graph showing temporal changes in the total sum value of subtraction images.

According to the above description, the apparatus sorts images into mask images and contrast images by using the delay time. However, this modification uses an electrocardiographic waveform (FIG. 7) and performs subtraction between an image as an initial characteristic wave, typically an image between R-waves, and an image after the second R-wave, whose electrocardiographic phases are nearest to each other. The total sum value of subtraction images changes for each frame in the manner shown in FIG. 8. A point where this change abruptly occurs can be determined as a point of time at which a contrast medium is injected. This determination can be performed by one of the following first and second methods.

The first method calculates the difference between the average value of several frames (e.g., five frames) in the past, as the total sum value of subtraction images after the second R-wave, and the value of the next frame, sets, as a start point, a point at which the difference value exceeds a predetermined threshold consecutively throughout three frames, and determines a point of time 0.5 sec preceding the start point as the start of the injection of a contrast medium (the start of contrast images).

The second method calculates the average value ($M_s$) of the total sum values of subtraction images of several frames (e.g., 15 frames) after the second R-wave, sets, as a start point, a point at which the values of three consecutive frames become smaller than a value ($M_s$−Th) which changes from the average value by a predetermined threshold (Th), and determines a point of time 0.5 sec preceding the start point as the start of the injection of a contrast medium (the start of contrast images).

(Fourth Modification)

According to the above description, the apparatus performs subtraction between the minimum value projection image of a mask image and the minimum value projection image of a contrast image, and extracts a blood vessel region (contrast region) by performing a threshold process with respect to the subtraction image. However, the S/N ratio is very low in a person with a large body thickness or in the direction of increasing body thickness (e.g., LAO60 or CAU30), and this method cannot properly extract a blood vessel region in some cases. In order to solve this problem, it suffices to perform, in a heart region, subtraction between each of contrast images and one of mask images which has a cardiac phase nearest to that of the contrast image, generate the minimum value projection image of the subtraction results, and extract a blood vessel region by performing a predetermined threshold process with respect to the minimum value projection image.

(Fifth Modification)

According to the above description, only a blood vessel region is extracted. However, it suffices to combine this technique with the invention disclosed in Jpn. Pat. Appln. KOKAI Publication No. 2004-112469, which extracts a body movement region and selects an optimal mask image on the basis of the degrees of coincidence up to the extracted region, and remove a contrast region from the body movement region, and calculate the degrees of coincidence upon localization to part of the remaining body movement region. That is, when selecting an optimal mask image from a plurality of mask images with respect to each contrast image, this technique uses the degree of similarity of a positional shift on an image due to the body movement of the subject as an index. However, it suffices to calculate the degree of similarity upon localization to part of the remaining body movement region obtained by removing a contrast region.

(Sixth Modification)

According to the above description, each of contrast images is compared with each of all mask images. This method is free from errors but takes much calculation time. In order to shorten the calculation time, it is preferable to compare mask images with contrast images upon narrowing down images to those near the cardiac phases of the contrast images. More specifically, if T represents a cardiac cycle and an arbitrary contrast image with an R-wave being the origin is at a cardiac phase t, comparison is performed by using only mask images within the range of t±T/6.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
an image generating unit which generates first X-ray images before injection of a contrast medium and second X-ray images after injection of the contrast medium;
a region detecting unit which detects a non-contrast region based on the first X-ray images and the second X-ray images;
a selecting unit which selects one of the first X-ray images with respect to each of the second X-ray images on the basis of a correlation between the first X-ray images in the non-contrast region and the second X-ray images in the non-contrast region; and
a subtraction image generating unit which generates subtraction images by performing subtraction between each of the second X-ray images and the selected one of the first X-ray images.

2. An apparatus according to claim 1, further comprising an operating unit which sets an acquisition time for the first X-ray images; and
a control unit which controls outputting of a contrast medium injection instruction at a point of time at which the set acquisition time has elapsed from the start of radiography performed by the image generating unit.

3. An apparatus according to claim 1, further comprising:
a setting unit which sets, as tentative images, some of the first X-ray images which are generated during at least one cycle of an electrocardiogram and are not influenced by the contrast medium;
a subtraction unit which generates second subtraction images with regard to different electrocardiographic phases by performing subtraction between each of the second X-ray images and one of the tentative images whose electrocadiographic phase is nearest to a phase of each of the second X-ray images; and a detecting unit which detects an injection timing of a contrast medium on the basis of changes in pixel values of said second subtraction images.

4. An apparatus according to claim 1, further comprising:
an image sorting unit which separates the second X-ray images into first contrast images and second contrast images, and wherein
the selecting unit selects the one of the first X-ray images with respect to each of the second X-ray images on the basis of correlations between the first contrast images in the non-contrast region and the first X-ray images in the non-contrast region, and
the subtraction image generating unit generates the subtraction images by performing subtraction between each of the first contrast image and the selected one of the first X-ray images.

5. An apparatus according to claim 4, wherein the image sorting unit separates the second X-ray images into first contrast images and the second contrast images before and after the start of movement of a bed top on which a subject is placed.

6. An apparatus according to claim 4, wherein the image sorting unit separates the second X-ray images into first contrast images and the second contrast images before and after the start of movement of at least one of a collimator and a compensation filter.

7. An apparatus according to claim 1, wherein the region detecting unit generates a first minimum value projection image from said first X-ray images by projection processing in a time axis direction, generates a second minimum value projection image from said second X-ray images, and detects the non-contrast region on the basis of a subtraction image between the first minimum value projection image and the second minimum value projection image.

8. An apparatus according to claim 1, wherein
the region detecting unit detects a body movement region which is within the non-contrast region and in which a body movement of the subject has occurred, and
the mask selecting unit obtains a correlation between the first X-ray images in the body movement region and the second X-ray images in the body movement region.

9. An image processing apparatus comprising:
a region detecting unit which detects a non-contrast region based on first X-ray images before injection of a contrast medium and second X-ray images after injection of the contrast medium which are generated by repeatedly radiographing a subject;
a selecting unit which selects one of the first X-ray images with respect to each of the second X-ray images on the basis of a correlation between the first X-ray images in the non-contrast region and the second X-ray images in the non-contrast region; and
a subtraction image generating unit which generates subtraction images by performing subtraction between each of the second X-ray images and the selected one of the first X-ray images.

10. A computer readable medium including computer executable code which when executed on a computer causes the computer to implement an X-ray diagnostic operation comprising:
generating first X-ray images before injection of a contrast medium and second X-ray images after injection of the contrast medium;
detecting a non-contrast region based on the first X-ray images and the second X-ray images;
selecting one of the first X-ray images with respect to each of the second X-ray images on the basis of a correlation between the first X-ray images in the non-contrast region and the second X-ray images in the contrast region; and
subtraction image generating which generates subtraction images by performing subtraction between each of the second X-ray images and the selected one of the first X-ray images.

* * * * *